United States Patent [19]
Ts'o et al.

[11] Patent Number: 6,080,726
[45] Date of Patent: Jun. 27, 2000

[54] ANTI-VIRAL AND IMMUNO STIMULATOR POLYNUCLEOTIDE DUPLEX AND USE THEREOF

[75] Inventors: Paul O. P. Ts'o, Lutherville; Laure Aurelian, Baltimore, both of Md.

[73] Assignees: University of Maryland; Johns Hopkins University, both of Baltimore, Md.

[21] Appl. No.: 07/946,023

[22] Filed: Sep. 11, 1992

Related U.S. Application Data

[63] Continuation of application No. 07/614,696, Nov. 19, 1990, abandoned, which is a continuation of application No. 07/368,156, Jun. 15, 1989, abandoned, which is a continuation of application No. 06/764,778, Aug. 12, 1985, abandoned.

[51] Int. Cl.$^7$ ..................................................... A61K 31/70
[52] U.S. Cl. .................................. 514/44; 514/23; 514/24
[58] Field of Search .................................. 514/44, 23, 24

[56] References Cited

U.S. PATENT DOCUMENTS

| | | | |
|---|---|---|---|
| 3,975,520 | 8/1976 | Chain et al. | 514/44 |
| 3,980,776 | 9/1976 | Ishida et al. | 514/44 |
| 4,024,222 | 5/1977 | Ts'o et al. | 514/44 |
| 4,603,131 | 7/1986 | Bernstein et al. | 514/20 |

OTHER PUBLICATIONS

Munk et al, Chemical Abstracts, vol. 77 (1972) No. 32470j. "Effect of poly I:C induced interferon on herpes virus hominis infection".

*The Merck Index* 9th ed., 1976, p. 137 No. 1059; p. 270, No. 2103; and p. 1202 No. 9046.

*Primary Examiner*—Elli Peselev
*Attorney, Agent, or Firm*—Cushman Darby & Cushman IP Group of Pillsbury Madison & Sutro LLP

[57] ABSTRACT

A method of treating HSV-2 infection which comprises administering to a host subject to said infection an effective amount of a polynucleotide of the formula polyrI.polyr$(C_{12}U)$ where n is an integer from 4 to 29. The polynucleotide is advantageously administered intranasally.

5 Claims, 6 Drawing Sheets

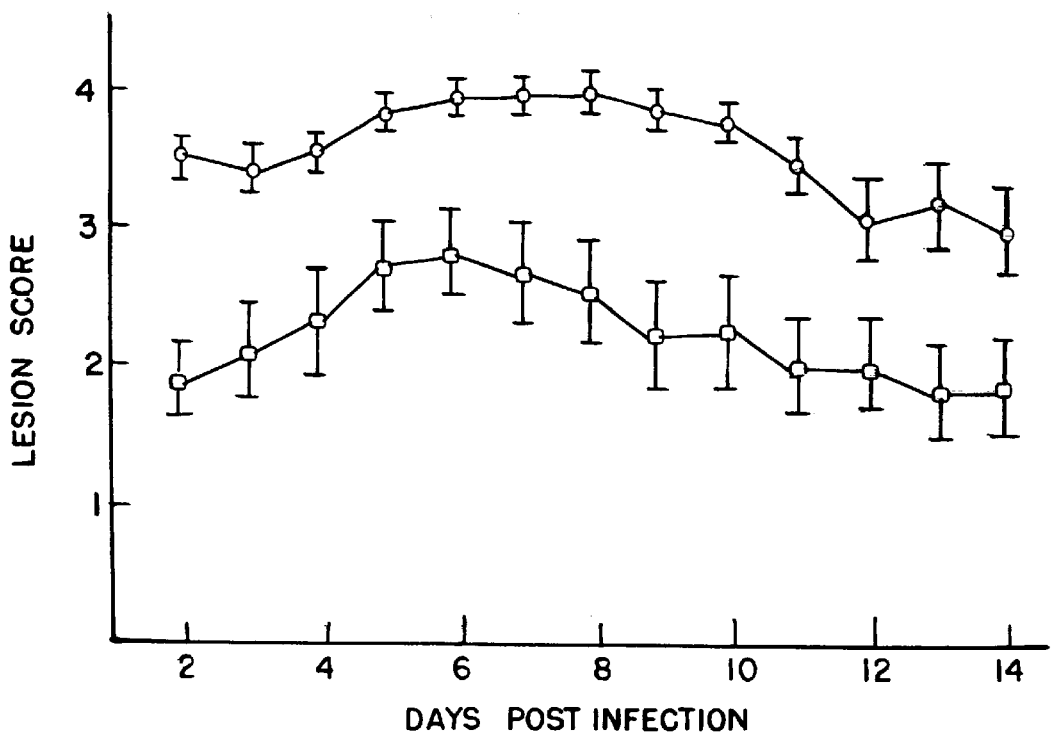
F I G. 6
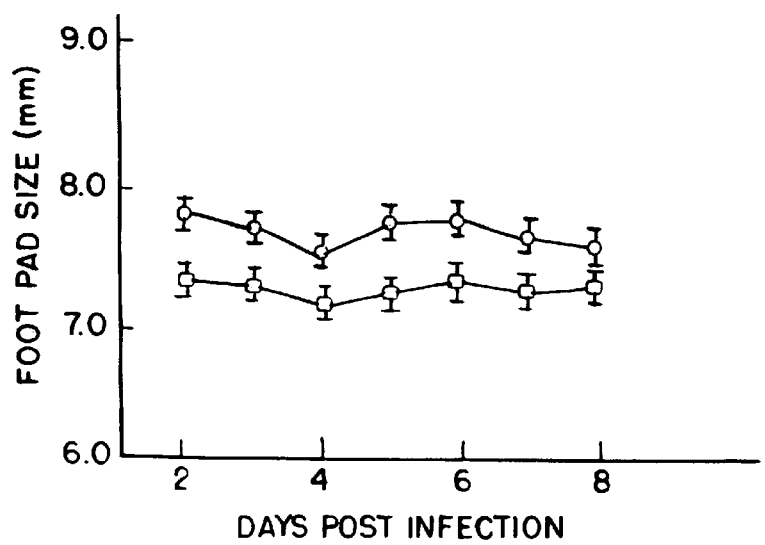
F I G. 7

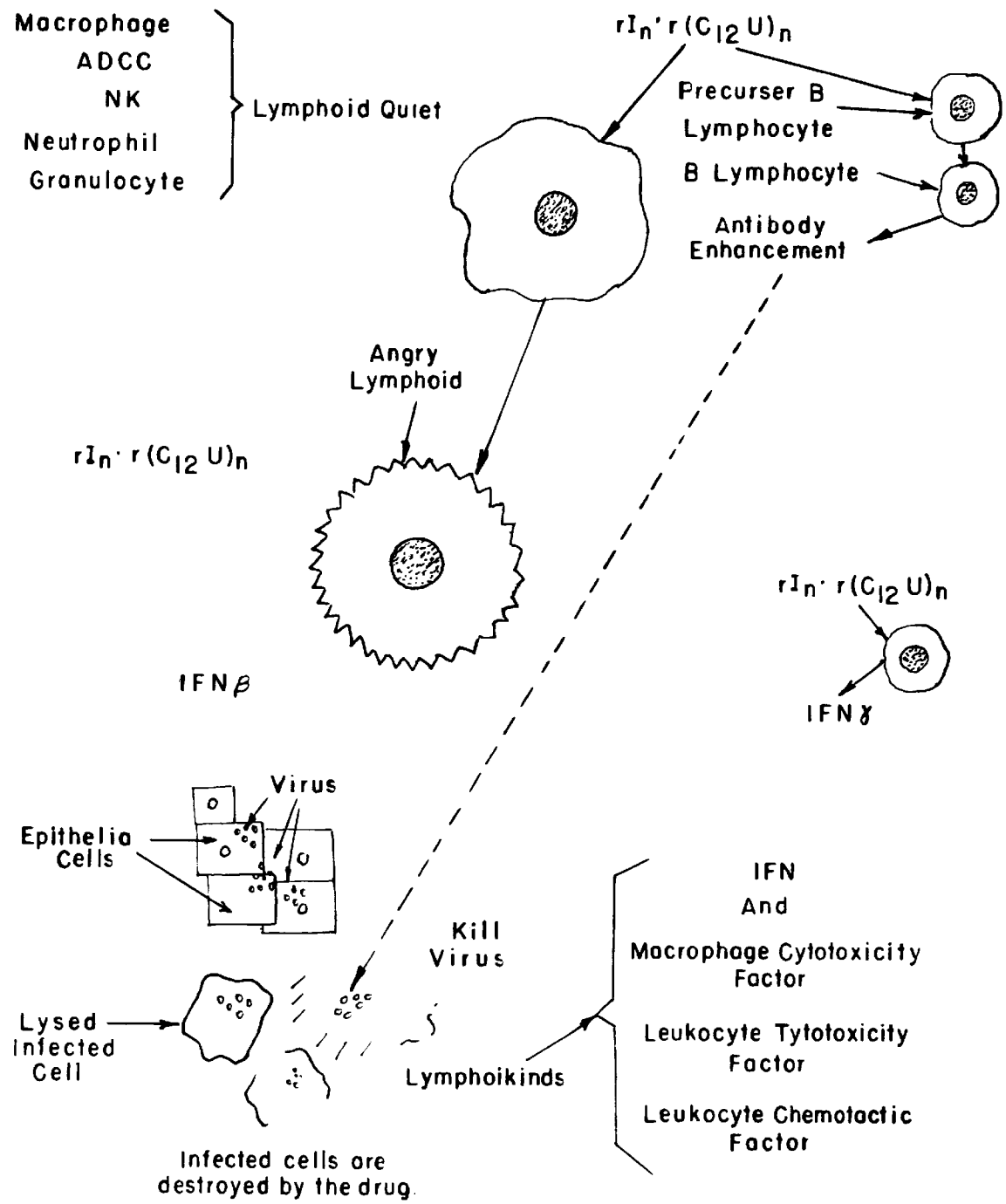
F I G. 10

ANTI-VIRAL AND IMMUNO STIMULATOR POLYNUCLEOTIDE DUPLEX AND USE THEREOF

This is a continuation of application Ser. No. 07/614,696, filed on Nov. 19, 1990, now abandoned, which was abandoned upon the filing hereof which is a continuation of Ser. No. 07/368,156, filed Jun. 15, 1989, now abandoned, which is a continuation of Ser. No. 06/764,778 filed Aug. 12, 1985, now abandoned.

This invention relates generally to therapeutic compositions of matter, and to methods for using polynucleotide duplexes to provide a defense system against viral diseases and for enhancing the immunological defense system of animals including human beings.

Herpes Simplex Virus (HSV) infections of the genital tract are increasing in incidence. Current reports indicate that the number of patients consulting for primary genital infections has increased from 30,000 in 1976 to 300,000 in 1979.

Based on these numbers, and on an estimated 50–75% recurrent rate for genital HSV-2 lesions, it can be calculated that each year, in the United States, there are 5–9 million cases of genital herpes. However, direct patient questioning suggests that primary infection often occurs following exposure to an asymptomatic host.

Indeed, the epidemiology of HSV-2 infections is affected by the interaction of three major factors: (1) the close antigenic relationship between type 1 (HSV-1), the virus that generally causes oral/facial lesions, and type 2 (HSV-2), the virus that generally causes genital lesions, (ii) the establishment of latency with the inherent risk of ensuing recurrent disease, and (iii) the effect of specific immune factors.

A study has now been made of the Herpes Simplex Virus (HSV), and a new method and drug has been provided which is a mismatched analog of $rI_n \cdot rc_n$, polyrI.polyr($C_{12}U$). It retains the ability to induce interferon but does not evidence cellular toxicity.

In vitro, the drug treatment of HSV-2 infected human fibroblasts results in 80% reduction in virus titers.

In vivo, antiviral activity was evaluated in a guinea pig model of recurrent HSV-2 infection. Guinea pigs were inoculated with HSV-2 and treated with intraperitoneal injections of polyrI.polyr($C_{12}$,U) or placebo (saline). They were followed for: (i) development and severity (lesion score) of primary disease and (ii) appearance and duration of recurrent episodes.

Animals first treated evidenced a significant reduction in the severity of the primary disease, and in the incidence of recurrent episodes. Similar results were obtained in animals treated i.p. and in those given intranasal doses. Experiments designed to elucidate the mechanism of in vivo action of the drug indicated that it: (i) causes a 3-fold reduction in virus titers at the site of infection, (ii) reduces 2–5 fold the titers of ganglionic virus, (iii) does not modify virus specific lymphocyte blastogenesis and titers of neutralizing antibody and (iv) causes a 2-fold enhancement of in vitro natural killer cell activity. This data indicates that the drug polyrI.polyr($C_{12}U$) may have both antiviral and immunomodulatory activities.

In the other mice models, the inoculation of HSV-2 induced fatal events. Injection of polyrI.polyr($C_{12}U$) compound can protect infected animals from fatality. The aged animal is much more suspectible to the virally induced fatality than the younger animal. Injection of polyrI.polyr ($C_{12}U$) compound affords the protection to the old animal against the virus as the aged animal now has the same resistance as the young animal. Immunological studies including NK cell activation indicated that polyrI.polyr ($C_{12}U$) compound produced immunological protection for the aged animal so that it now becomes immune to the virally induced fatality. This study indicates the polyrI.polyr ($C_{12}U$) compound can stimulate the immunal defense system of aged animal including humans against viral diseases.

Still another object of this invention is to provide a polynucleotide duplex which can be used to combat viral diseases, and which has sterility and shelf life until such polynucleotide is utilized to treat a subject.

An object of this invention is to provide a polynucleotide duplex and method for use thereof in providing a defense system against viral diseases and in enhancing the immunological defense system of animals including humans.

Still another object of this invention is to provide a polynucleotide duplex and process for use thereof in stimulating the immunal defense of aged or otherwise compromised including humans.

And even another object of this invention is to provide a polynucleotide duplex and method for use thereof in controlling and minimizing herpes virus in animals including humans.

Still even another object of this invention is to provide a method for using a polynucleotide duplex in providing a defense system against viral diseases and in enhancing the immunological defense system of animals including humans.

Still another object of this invention is to provide a method for utilizing a polynucleotide duplex for stimulating the immunal defense of aged or otherwise compromised including humans.

Still even another important object of this invention is to provide a method and a chemical complex for use against viral diseases including the common cold, herpes, AIDS (disease syndrome) arthritis, and chicken pox, and similar disease.

And another object of this invention is to provide a method and composition for stabilizing as well as enhancing the immunological defense system of human being, particularly the elderly.

BRIEF DESCRIPTION OF THE DRAWINGS

FIG. 6 is a graphical representation of lesion score versus days post infection;

FIG. 7 is a graphical representation of foot pad size (mm) versus days post infection;

FIG. 10 is a sketch showing the effect of the drug polyrI.polyr($C_{12}U$) on undesirable viruses.

Figure 1:
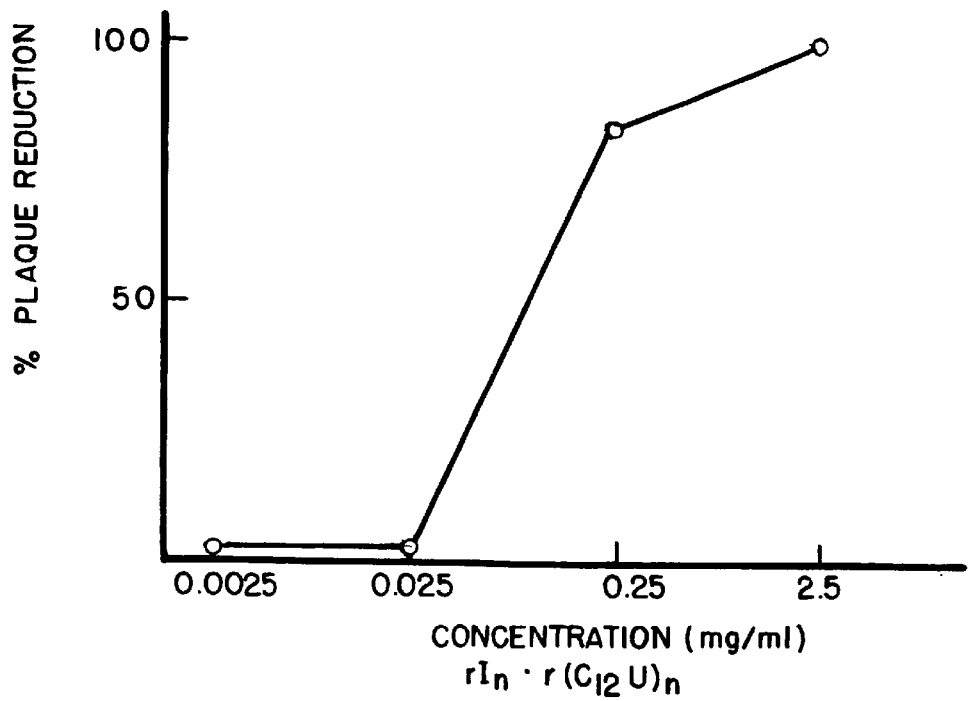
FIG. 1 is a graphical representation of percentage plaque production versus concentration of the drug polyrI.polyr ($C_{12}U$)

| | LEGEND |
|---|---|
| ADCC | Antibody dependent cell cytotoxicity |
| FCS | Fetal calf serum |
| HSV | Herpes simplex virus |
| IFN | Interferon |
| IL | Intralesional doses |
| IN | Intranasally |
| IP | Intraperitoneally |
| K | An immuned lymphoid cell |
| MEM | Minimal essential medium |
| MHRF | Human foreskin fibro blasts cells |
| NK | Natural killer |
| PBL | Peripheral blood lymphocytes |
| PBS | Phosphate buffered saline |
| PFU | Plaque forming units |
| RPMI | Tradename for a medium (RPMI - 1640) |
| SEM | Standard error about the mean cells |

DISCUSSION OF THE INVENTION

Double stranded RNAs are potent biologic modifiers. Animal studies using $rI_n \cdot rC_n$ as the prototype double stranded RNA have shown that it is effective against influenza and vaccinia virus infections (1)(the numeral refers to the prior art references listed at the end hereof), and in rhabdoviral neuritis (2,3) when administered prophylactically. Effectiveness was also demonstrated against rabies (4) and against arboviral (5) enteroviral (1.6) and Herpes simplex virus type 1 (HSV-1), (1,6,7) encephalitis when administered within 4 days of infection.

In humans, local $rI_n \cdot rC_n$ application was shown to cause a definite improvement in HSV-1 keratitis (8–10), and some reduction in the duration of herpetic disease following intravenous administration (11). However, the potential of $rI_n \cdot rC_n$ as a chemotherapeutic agent has been limited by the very severe and extensive toxic side effects encountered in all the studies in which it was administered parenterally (reviewed in 12,13).

The findings described in this patent application were made possible by the development of a mismatched polynucleotide duplex polyrI.polyr($C_{12}U$) that is significantly less toxic than $rI_n \cdot rC_n$. While retaining the ability to induce interferon (IFN) synthesis and protect against lethal viral challenge (Semliki Forest virus) (13). Semliki Forest sought to define the chemotherapeutic potential of polyrI.polyr ($C_{12}U$) against HSV (HSV type 2 (HSV-2), a common sexually transmitted disease, that is characterized by the ability of the virus to persist in sensory ganglia (15–19) causing periodic recurrent episodes. The experimental design was based on previous findings indicating that virus specific and non-specific (reviewed in 16,20) immunity plays a significant role in herpetic disease.

It is demonstrated that polyrI.polyr($C_{12}U$) (See references 40 and 41 U.S. Pat. No. 4,024,222 issued May 17, 1977 and U.S. Pat. No. 4,103,641 issued Dec. 13, 1978) administration causes a significant reduction in the incidence and severity of HSV-2 induced primary and recurrent disease when administered intra peritoneally (IP) or intranasally (IN). Virus titers at the focus of infection and in the sensory ganglia are significantly decreased in polyrI.polyr($C_{12}U$) as compared to placebo treated animals, while NK activity is significantly enhanced.

The materials and methods will now be described. The cells and virus will now be considered. African green monkey kidney (Vero) and human newborn foreskin fibroblasts (MRHF) cells (Whittaker, M. A. Bioproducts, Walkersville, Md.) were grown in Eagle's minimal essential medium (MEM) with 10% fetal calf serum (FCS) and 25 mM Hepes (N-2-hydroxyethylpiperazine-N'-2-ethanesulfonic acid) buffer. Guinea pig lung fibroblasts (JH4 clone 1, American Type Culture Collection) were grown in medium F12 (Whittaker, M. A. Bioproducts) with 10% FCS. A single stock of the G strain of HSV-2, the isolation and properties of which were previously described (21) was used throughout.

Female Hartley strain guinea pigs (Charles River, Wilmington, MA) weighing 300–350 g each, and 6–8 week old male Swiss Webster mice (Charles River) were injected subcutaneously in the right hind footpad with $1-2 \times 10^5$ PFU of HSV-2. Swiss Webster mice were also injected with $2 \times 10^5$ PFU of HSV-2 intradermally in the chest or in the pinna of the right ear (17). Animals were monitored daily for the development of skin lesions, neurological complications (paralysis), encephalitis and death. Skin lesions were scored blindly by two independent observers according to an arbitrary severity scale in which 1=slight erythema or healing vesicles; 2=moderate erythema with swelling; and 3=severe erythema and swelling with vesicles. Results were expressed as mean values±Standard error about the mean (SEM). A second criterion of disease severity was the size of the infected footpad. It was measured with calipers (Mitutoyso, Tokyo, Japan) and compared to the size of the uninfected rear footpad.

Administration of polyrI.polyr($C_{12}U$). The synthesis and properties of the mismatched analogue of polyinosinic-polycytidylic acid duplex polyrI.polyr($C_{12}U$) were previously described (13,14). For use in these studies it was reconstituted (25 mg/ml) in sterile distilled water. Administration was initiated at various times post infection (p.i.) and all animals received 3 or 4 additional doses given at 48 hrs. intervals as stated. Toxicity, defined as pyrogenicity, weight loss, listlessness and mortality were not observed in any one of the animals studied in these series, nor in uninfected mice given 5 doses (400 ug each) of polyrI.polyr ($C_{12}U$) intranasally at 48 hrs. intervals (data not shown).

The virus isolation and titration will now be considered. Ten-fold dilutions of vesicular fluid from skin lesions, were inoculated onto monolayers of Vero cells in microtiter wells (Falcon 2040). The cells were harvested 10 days later and the infectious units determined by plaque assay on MRHF cells under a 2% methyl cellulose (4000 cps) overlay (22). Ganglia corresponding to the injected area (footpad: lumbosacral; ear:cervical 4,5 and 6 and trigeminal; chest:cervical 1, 2 and 3) were collected from latently infected mice at 34 days p.i. They were co-cultured on confluent monolayers of Vero cells in 16 mm wells (Costar, Cambridge, Mass.) for 24 days, frozen and thawed and assayed on MRHF cells as described (15).

The neutralization of the virus is now described. HSV antibody was assayed by the plaque reduction multiplicity analysis and the extent of virus neutralization was expressed as K values as previously described (23). For comparative purposes, assays were performed simultaneously with the same virus preparations.

The lymphocytes collection will now be described. Peripheral blood lymphocytes (PBL) were prepared from heparinized blood (20 U/ml; Upjohn Co., Kalamazoo, MI), mixed with equal volumes of calcium and magnesium-free phosphate buffered saline (PBS) and centrifuged (800× g; 30 min.) on a Ficoll-metrizoate gradient as described (18, 24, 25). Mononuclear cells were collected from the interface. Platelets were removed by washing three times with medium RPMI 1640 at low speed for 2 min.

The lymphocyte proliferation assay will now be described. PBL ($2\times10^6$/ml) were cultured at 37° C. in freshly made RPMI 1640 medium with 10% decomplemented normal guinea pig serum, 25 mM Hepes buffer, $5\times10^{-5}$ M-B-mercaptoethanol, 10 U of mycostatin and 50 µg of gentamycin per ml as previously described (18,24,25). Cultures (1-ml volume) were set in snap-cap tubes (12 by 75 mm; Falcon 2054) in the presence of viral antigen (12.5 µg protein/ml) prepared as previously described (18) or PBS control. At 6 days in culture, cells were suspended by blending in a Vortex mixer, and samples (100 µl) were transferred in triplicate to microtiter wells (Falcon 2040). Cells were pulsed for 4 hrs. at 37° C. with 25 µl of tritiated thymidine [($^3$H-TdR); 40 µCi/ml/well] and harvested onto glass fiber filters (Reeve Angel grade 934 AH). Results were expressed as net cpm=(mean cpm experimental)–(mean cpm PBS control). Based on previous findings with mock antigen prepared from uninfected cells (25), a response was considered positive if it registered>200 net cpm.

The natural killer (NK) assay is an now described. Target cells were the rhesus monkey cell line MA104 (Whittaker, M. A. Bioproducts) "mock" infected with PBS or infected with HSV-2 for 4 hrs. Cells ($5-20\times10^6$) were labeled for 1 hr. with 100 µCi of $^{51}$Cr (as NaCrO4; Amersham, Arlington Heights, Ill) at 37° C., washed three times, resuspended in RPMI 1640 with 10% heat inactivated FCS and dispensed ($1\times10^4$ cells/50 ul) in conical bottom microtiter plates (Dynatech, Alexandria, VA) immediately before effector cells were added. Microtiter plates were centrifuged from 5 min. at 75× G and incubated for 4 hrs. at 37° C. in a 5% $CO_2$ atmosphere. The supernatants were harvested using the Titertek Supernatant Collection System (Flow Laboratories, McLean, Va.) and the radioactivity was determined with a Beckman 5500 gamma counter. The $^{51}$Cr release was calculated according to the formula:

$$\text{Percent Specific Lysis} = \frac{\text{Experimental cpm} - \text{Spontaneous cpm}}{\text{Maximum cpm} - \text{Spontaneous cpm}} \times 100$$

where spontaneous release was obtained from target cells incubated in medium and maximum release was obtained from target cells incubated (37° C., 4 hrs.) with 1% Triton-X 100. Spontaneous release values for infected or uninfected MA104 cells were always less than 12%.

The NK enhancing activity assay will now be considered. Triplicate samples of NK effector cells ($4\times10^5$ cells/microtiter well) were incubated for 2 hrs. at 37° C. in 50 µl of polyrI.polyr($C_{12}$U) or interferon (IFN). $^{51}$Cr labeled MA104 targets ($10^4$/well) were added directly to the wells, to give an E:T ratio of 80:1. The plates were incubated at 37° C. for 4 hrs. and the supernatants were harvested and counted. $^{51}$Cr labeled MA104 targets incubated with polyrI.polyr($C_{12}$U) or IFN in the absence of effector cells served as a negative control. Radioactivity values in the negative controls were similar to the spontaneous release values. The enhancement of NK activity was calculated according to the formula:

$$\% \text{ NK Enhancement} = 1 - \frac{\% \text{ Specific Lysis Effector cells}}{\% \text{ Specific Lysis Effector cells} + \text{supernatant}} \times 100$$

In this assay the percent specific lysis by effector cells averaged 24.2±3.

The preparation of guinea pig NK enhancing factor(s) will now be considered. Guinea pig lung fibroblasts (JH4 clone 1) were exposed to 2.5 mg/ml of polyrI.polyr($C_{12}$U) for 24 hours and the supernatants [incubated for 30 min. at 70° C. to inactivate the polyrI.polyr($C_{12}$U) were assayed for antiviral activity on JH4 cells infected with vesicular stomatitis virus (VSV)/cell as described (13,14). The assays were performed in triplicate, and each plate contained an uninfected cells control, and a VSV-infected cell control. The antiviral activity in the JH4 culture supernatants was probably due to IFN, since it was resistant to pH2.0 and sensitive to trypsin (data not shown).

Figure 2:
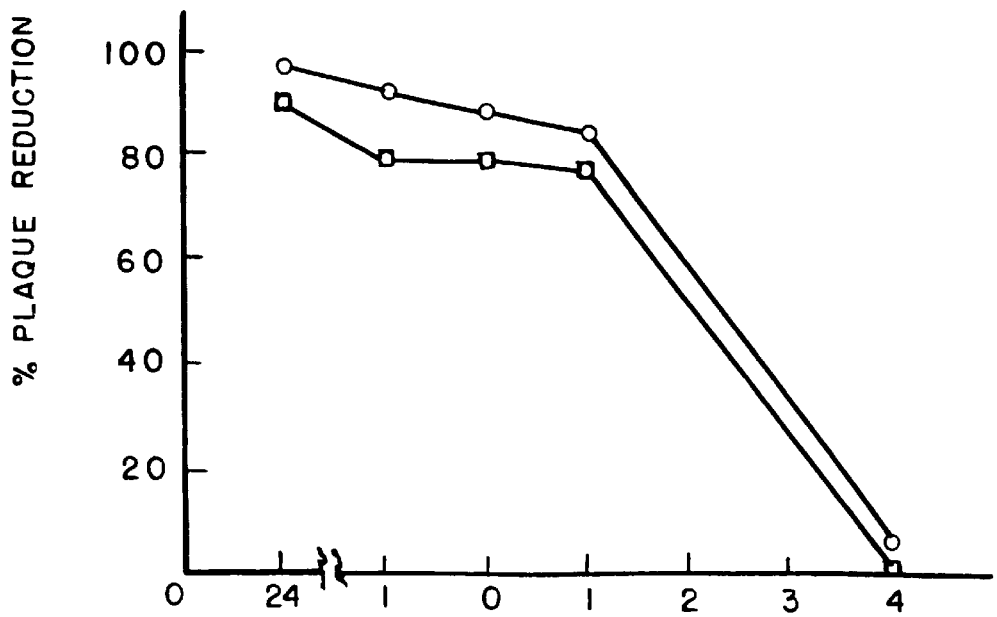
FIG. 2 is a graphical representation of the percentage of plaque versus time.

The results of polyrI.polyr($C_{12}$U) inhibits HSV-2 growth in vitro. Previous studies had shown that polyrI.polyr($C_{12}$U) inhibits the growth of some RNA viruses in vitro (13). To verify its effect on HSV-2 growth, MRHF cells were treated with increasing concentrations (0.0025–2.5 mg/ml) of polyrI.polyr($C_{12}$U) for 60 min. or "mock" treated with PBS at various times before or after infection and virus titers were determined 48 hrs. later. As shown in FIGS. 1 and 2, pretreatment of MHRF cells with 0.25 and 2.5 mg/ml of polyrI.polyr($C_{12}$U) caused a significant reduction (89–100% respectively) in virus titers as compared to cells "mock" treated with PBS (FIG. 1). A similar reduction was observed in cells exposed to polyrI.polyr($C_{12}$U) at the time of infection or at 1 hr. p.i., but not thereafter (FIG. 2).

The therapeutic effect of polyrI.polyr($C_{12}$U) on primary HSV-2 disease will be discussed. The effect of IP treatment with polyrI.polyr($C_{12}$U) on HSV-2 encephalitis was studied in mice infected with HSV-2 ($2\times10^5$PFU) in the footpad beginning at 6 hrs. p.i. At 3–4 weeks p.i. 7/14 (50%) placebo treated animals developed paralysis and died. All 14 polyrI.polyr($C_{12}$U) treated mice remained free of disease ($p<0.01$).

The effect of polyrI.polyr($C_{12}$U) treatment on primary HSV-2 induced skin lesions was studied in the guinea pig model (22–24). Animals were treated with polyrI.polyr ($C_{12}$U) (5 or 10 µg/g weight) or saline (placebo) by IP inoculation beginning at 4 hrs. before infection with HSV-2, or at 8, 20 and 48 hrs. p.i. They were scored for disease severity based on lesion score and footpad size. At 10 µg/g weight, polyrI.polyr($C_{12}$U) treatment did not affect the proportion of animals with clinical symptons, the duration of the lesions or their severity, as set forth in Table 1. On the other hand, at 5 µg/g weight polyrI.polyr($C_{12}$U) treatment at −4, 8 or 20 hrs. p.i. reduced the incidence of disease and the severity and duration of the symptoms as indicated in Table 1.

Figure 3:
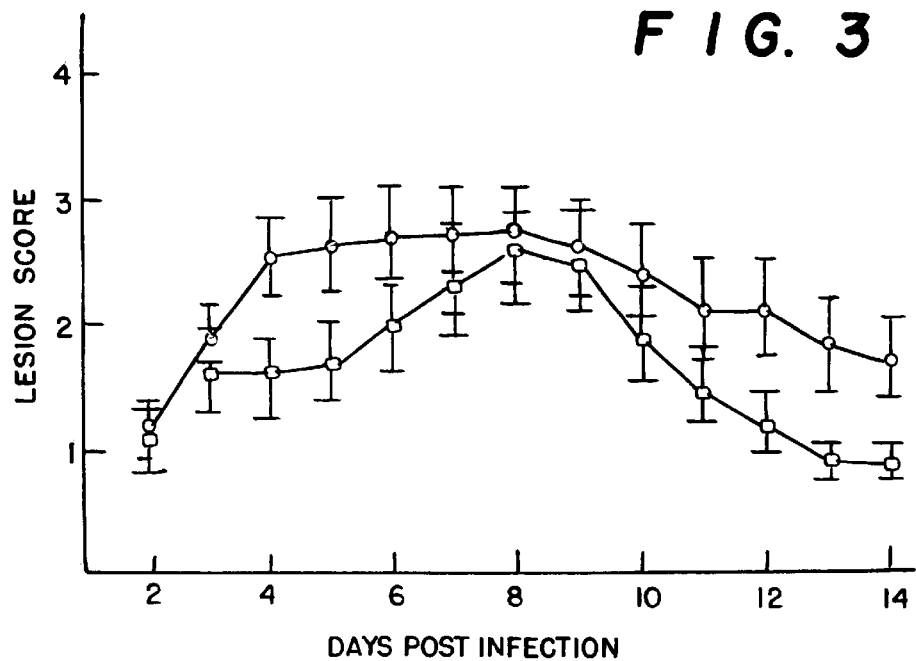
FIG. 3 is a graphical representation of lesion score versus days post infection.
Figure 4:
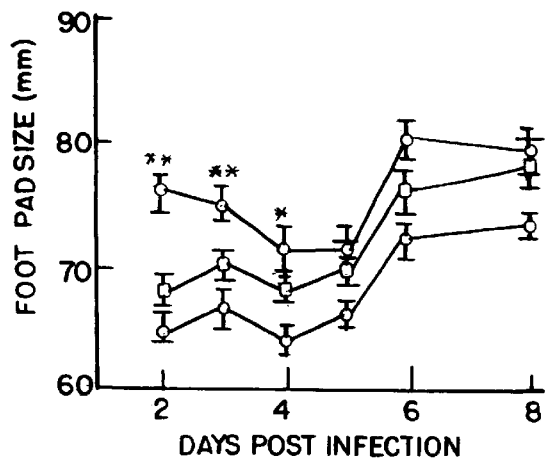
FIG. 4 is a graphical representation of foot pad size (mm) versus days post infection.
Figure 5:
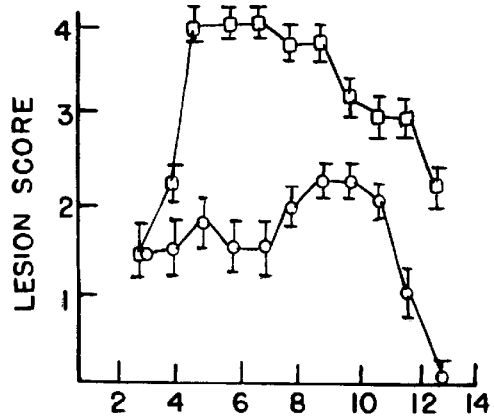
FIG. 5 is a graphical representation of lesion score versus days post inoculation.

The temporal effect of polyrI.polyr($C_{12}$U) treatment (5 µg/g weight; IP) on the outcome of HSV-2 induced skin lesions is shown in FIGS. 3, 4 and 5. In the placebo groups clinical symptoms were first detected at 3 days p.i. with 50% of the animals displaying severe clinical symptoms by day 5–6 p.i. The average lesion score was maximal at this time. It remained at this level until day 9 p.i. and did not return to pre-infection levels as late as 14 days p.i. On the other hand, animals treated beginning at 8 (FIG. 5) or 20 (FIG. 3)

TABLE 1

Effect of dose and time of PolyrI. polyr ($C_{12}U$) treatment initiation on primary HSV-2 skin lesions

| Treatment[a] | Time (hrs) | Dose (μg/g) | No./total % | Primary skin lesions Duration (days ± SEM) | Lesion score ± SEM (day 6 p.i.) |
|---|---|---|---|---|---|
| polyrI. polyr ($C_{12}U$) | −4 | 10 | 8/10 (80%) | 9.0 ± 0.5 | 3.0 ± 0.5 |
| Placebo | −4 | — | 9/10 (90%) | 11.0 ± 0.6 | 3.3 ± 0.6 |
| polyrI. polyr ($C_{12}U$) | 20 | 10 | 8/10 (80%) | 10.0 ± 0.6 | 2.4 ± 0.6 |
| polyrI. polyr ($C_{12}U$) | −4 | 5 | 6/10 (60%) | 7.0 ± 0.1 | 2.0 ± 0.6 |
| polyrI. polyr ($C_{12}U$) | 20 | 5 | 16/21 (76%) | 7.4 ± 0.6 | 2.0 ± 0.4 |
| Placebo | 20 | — | 20/21 (95%) | 8.8 ± 0.7 | 2.7 ± 0.4 |
| polyrI. polyr ($C_{12}U$) | 8 | 5 | 4/6 (66.7%) | 11.3 ± 0.48[b] | 1.7 ± 0.60 |
| polyrI. polyr ($C_{12}U$) | 48 | 5 | 5/6 (83.3%) | 13.2 ± 0.40 | 2.7 ± 0.60 |
| Placebo | 8 | — | 5/6 (83.3%) | 13.8 ± 0.20 | 3.3 ± 0.7 |

[a]Guinea pigs infected with HSV-2 (1 × 10$^5$ PFU) in the footpad were given a total of 4 IP injections of polyrI. polyr ($C_{12}U$) (5 or 10 μg/g weight) or saline (placebo) beginning at 4 hrs. before infection (−4) or at 8, 20 and 48 hrs. p.i. All animals received 3 additional injections of equal doses at 48 hrs. intervals.
[b]Experimental group significantly different from placebo by one way analysis of variance (p < 0.001).

hrs. p.i. evidenced a significant delay in the appearance of severe lesions, such that at 4 days p.i., they were still virtually free of clinical symptoms. Furthermore, severe lesions resolved rapidly and lesion scores returned to normal levels at 12 days p.i. Essentially similar results were obtained using the footpad size as a criterion of disease severity. As shown in FIG. 4 for animals treated beginning at 20 hrs. p.i., the average footpad size at 2–3 days p.i., was significatnly (p<0.01) smaller in the treated as compared to the placebo group. Furthermore, the average footpad size of the treated but not the placebo animals returned to normal levels at 12 days p.i. (data not shown).

The second series of experiments relating to the effect of polyrI.polyr($C_{12}U$) therapy on primary HSV-2 skin lesions sought to define the effect of the route of polyrI.polyr($C_{12}U$) administration. Guinea pigs were infected with HSV-2 in the footpad and given a total of 5 IN doses (1.5 μg/g weight) of polyrI.polyr($C_{12}U$) beginning at 6 hrs. p.i. or 4 intralesional (IL) doses beginning at 8 hrs. p.i. All subsequent doses were given at 48 hrs. intervals. The proportion of animals with primary disease and the duration of the lesions were significantly (p<0.05) reduced in animals treated with polyrI.polyr($C_{12}U$) by the IN route (16/20 animals; 9.6±0.96 days) as compared to the placebo group (21/21 animals; 14.9±0.8 days). However, IL injection of polyrI.polyr($C_{12}U$) did not significantly alter the course of the HSV-2 induced primary disease as indicated in Table 2.

As shown in FIGS. 6 and 7, IN polyrI.polyr($C_{12}U$) administration caused a significant reduction in disease severity as determined by lesion score (FIG. 6) and foot size (FIG. 7) (p<0.01 by a one way analysis of variance). Thus, the placebo group evidenced severe lesions (av. score= 2.5±0.1) at 2 days p.i. and symptoms lasted for at least 14 days (av. score=1.9±0.3). On the other hand, the treated group remained free of symptoms except for mild lesions (av. score=1.5±0.3) on days 5–6 p.i. The clinical appearance of the lesions is shown in FIGS. 6 and 7 for animals examined at 6 days p.i. FIG. 6 shows a placebo treated animal presenting with erythema, slight edema, hemorrhage, and large vesicular lesions (lesion score=3). The IN treated animal presenting only with slight edema and assigned a lesion score of 1 is shown in FIG. 7.

It is noted that the polyrI.polyr($C_{12}U$) treatment of primary lesions reduces the incidence of recurrent disease. The effect of polyrI.polyr($C_{12}U$) treatment of primary HSV-2 lesions on the development of subsequent recurrent episodes was studied in the guinea pig model of recurrent disease (18,24,25). Animals infected with HSV-2 in the footpad were treated with polyrI.polyr($C_{12}U$) or placebo (saline) ad described above and monitored for recurrent disease for 3–4 months following resolution of the primary lesion. The proportion of animals with recurrent disease was significantly lower in the polyrI.polyr($C_{12}U$) treated as compared to the placebo groups independent of the route of polyrI.polyr($C_{12}U$) administration as

TABLE 2

Effect of route of polyrI. polyr ($C_{12}U$) administration on primary HSV-2 skin lesions[a]

| Treatment[a] | Route | Dose (μg/g) | No./total % | Primary skin lesions Duration (days ± SEM) | Lesion score ± SEM (day 6 p.i.) |
|---|---|---|---|---|---|
| polyrI. polyr ($C_{12}U$) | IP | 5 | 4/6 (66.7) | 11.3 ± 0.48 | 1.4 ± 0.6 |
| Placebo | IP | — | 5/6 (83.3) | 13.8 ± 0.2 | 3.0 ± 0.7 |
| polyrI. polyr ($C_{12}U$) | IL | 1.5 | 5/6 (83.3) | 9.6 ± 3.5 | 3.5 ± 0.50 |
| Placebo | IL | — | 5/5 (100) | 8.5 ± 2.9 | 3.8 ± 0.20 |
| polyrI. polyr ($C_{12}U$) | IN | 1.5 | 16/20 (80)[b] | 9.6 ± 0.96[c] | 1.8 ± 0.31[c] |
| Placebo | IN | — | 21/21 (100) | 14.9 ± 0.80 | 3.0 ± 0.6 |

[a]Guinea pigs infected with HSV-2 (1 × 10$^5$ PFU) in the footpad were given a total of 4 doses of polyrI. polyr ($C_{12}U$) (1.5 or 5 μg/g weight) or saline (placebo) beginning at 8 hrs. p.i. (IP route) or 6 hrs. p.i. (IL and IN routes). All animals received 3 additional doses at 48 hrs. intervals.
[b]Experimental group significantly different from placebo by chi square analysis (p < 0.05).
[c]Experimental group significantly different from placebo by one way analysis of variance (p < 0.001).

shown in Table 3.

Thus, only 9/21 (42.9%) animals treated by the IP route beginning at 20 hrs. p.i. and 11/20 (55%) of IN treated animals evidenced recurrent disease as compared to 18/21 (85.7%) and 17/18 (94%) animals in the respective placebo groups (p<0.01). The duration and severity of the recurrent episodes were not modified, but the frequency of recurrent disease and therefore the total number of episodes/animal were reduced in the polyrI.polyr($C_{12}U$) as compared to placebo treated animals as noted in Table 3.

The effect of polyrI.polyr($C_{12}U$) treatment of recurrent disease on subsequent recurrent episodes will now be explained. Guinea pigs were treated with polyrI.polyr($C_{12}U$) (17 animals) or placebo (6 animals) at the onset (day 1) of a recurrent episode and monitored (3 months) for subsequent recurrent symptoms. While there was a slight increase in the proportion of animals free of subsequent recurrent disease in the treated [5/17 (29%)] as compared to the placebo [1/6 (17%)] group, the two groups did not differ with respect to the number of post treatment recurrent episodes, their duration (9.1±1.7 and 9.0±2.8 days for polyrI.polyr($C_{12}U$) and placebo respectively) or severity (lesion scores=2.7 and 2.2 for the treated and placebo respectively).

The polyrI.polyr($C_{12}U$) treatment reduces virus titers in skin lesions and ganglia. The effect of polyrI.polyr($C_{12}U$) treatment on virus replication at the site of infection was determined in the guinea pig model. Virus titers in vesicular fluids from primary skin lesions (25±8 PFU) were significantly (p<0.05)

TABLE 3

Effect of polyrI. polyr ($C_{12}U$) treatment on the development of recurrent HSV-2 skin lesion[a]

| Treatment | Time (hrs) | Route | Dose ($\mu g/g$) | Recurrent disease No./total (%) | Duration (days ± SEM) | No. episodes/ animals |
|---|---|---|---|---|---|---|
| polyrI. polyr ($C_{12}U$) | 20 | IP | 5 | 9/21 (42.9)[b] | 5.7 ± 1.3 | 1.2 |
| Placebo | 22 | IP | — | 18/21 (85.7) | 5.8 ± 0.7 | 2.2 |
| polyrI. polyr ($C_{12}U$) | 8 | IP | 5 | 2/6 (33) | 3.0 ± 0 | 1.5 |
| Placebo | 8 | IP | — | 5/6 (83) | 4.0 ± 0.4 | 2.2 |
| polyrI. polyr ($C_{12}U$) | 6 | IL | 1.5 | 3/5 (60) | 5.8 ± 1.4 | 1.7 |
| Placebo | 6 | IL | — | 5/5 (100) | 8.0 ± 1.1 | 2.2 |
| polyrI. polyr ($C_{12}U$) | 6 | IN | 1.5 | 11/20 (55)[b)] | 4.0 ± 1.0 | 1.5 |
| Placebo | 6 | IN | — | 17/18 (94) | 6.7 ± 2.4 | 2.7 |

[a]Guinea pigs infected with HSV-2 (1 × 10$^5$ PFU) in the footpad were given a total of 4 doses of polyrI. polyr (1.5–5 $\mu g/g$ weight) or saline (placebo) by different routes. They were followed for the development of recurrent lesions for 3–4 months following resolution of the primary lesion.
[b]Experimental group significantly different from placebo by chi square analysis (p < 0.01).

lower in polyrI.polyr($C_{12}U$) treated (IP route) than untreated (72±18 PFU) animals.

Figure 8:
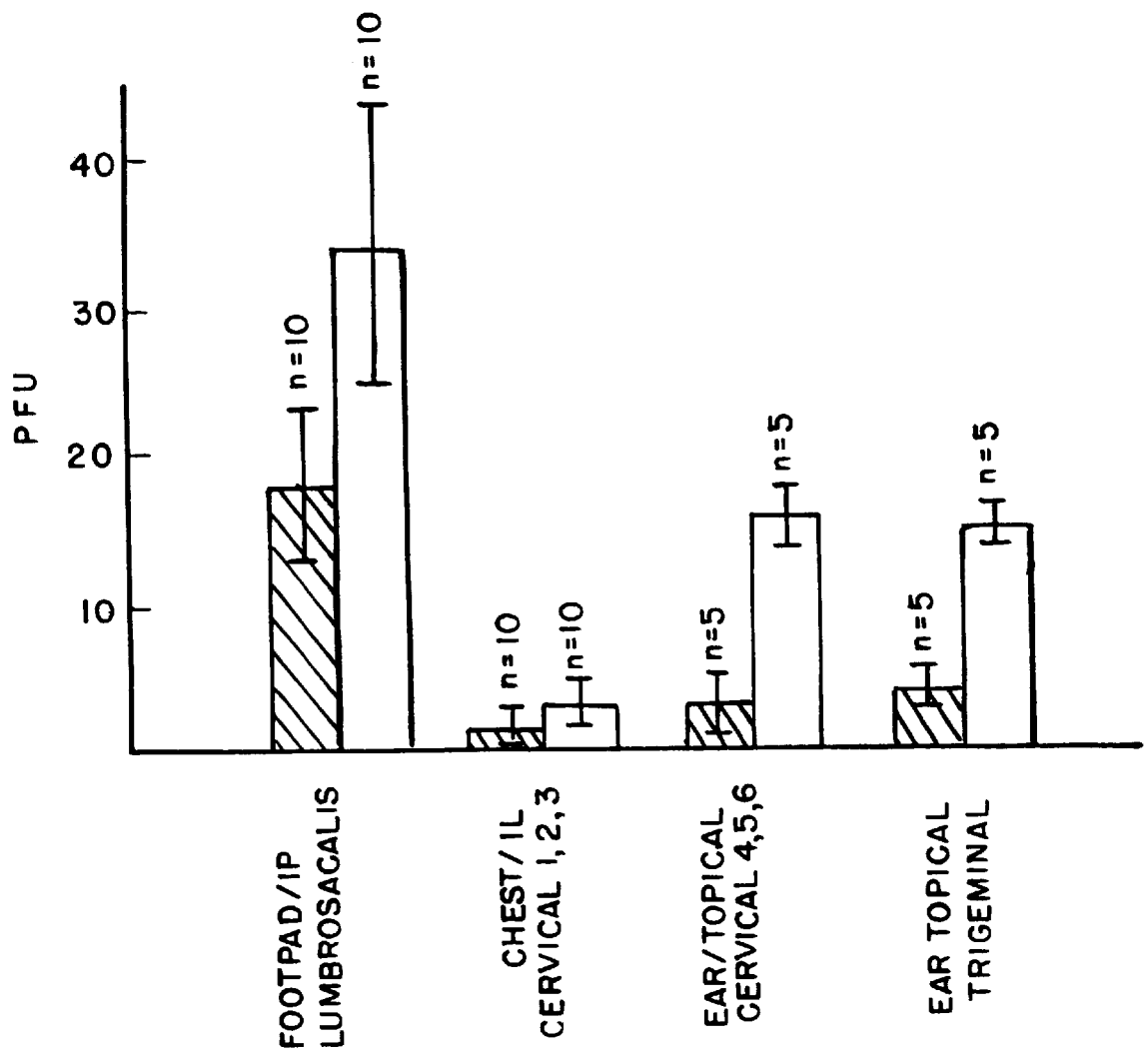
FIG. 8 is a graphical representation of PFU versus footpad/IP, chest/IL, ear/Topical(cervical 4, 5, 6), and ear/Topical (triminal)

The effect of treatment on ganglionic latency was studied in the mouse model. In the placebo treated groups, highest virus titers were observed in the lumbosacral ganglia obtained at 34 days p.i. from animals infected with HSV-2 in the footpad. Lowest titers were observed in cervical ganglia 1, 2 and 3 from animals infected with HSV-2 in the chest area. However, in all but the last group, the titers of ganglionic virus were significantly decreased by polyrI.polyr($C_{12}U$) treatment (FIG. 8). This was particularly evident in animals infected in the pinna of the ear and treated by topical application (p<0.01).

The effect of polyrI.polyr($C_{12}U$) on the development of virus specific immune memory is now discussed. Virus specific antibody and HSV-2 induced T cell proliferation of immune PBL were studies in polyrI.polyr($C_{12}U$) (5 $\mu g/g$ weight; IP) and saline treated guinea pigs. Antibody titers were similar in both groups (K=0.21±0.04 and 0.23±0.05). Similarly, the two groups did not differ with respect to the ability to mount an HSV-2 induced proliferative response [28,322±16,973 and 24,387±10,712 for placebo and polyrI.polyr($C_{12}U$) respectively].

The polyrI.polyr($C_{12}U$) treatment enhanced NK activity. The effect of in vivo or in vitro exposure to polyrI.polyr ($C_{12}U$) on NK activity was studied in the guinea pig model. PBL were obtained from groups of 7 HSV-2 infected guinea pigs treated with polyrI.polyr($C_{12}U$) or placebo by the IN route. They were assayed for NK activity against "mock" and HSV-2 infected targets. PBL from polyrI.polyr($C_{12}U$) treated animals evidenced a higher NK activity against both "mock" infected (% sp. lysis=27.7±7.0) and HSV-2 infected (% sp. lysis=32±4.7) targets than those from placebo treated animals (% sp. lysis=23.1±2.6 and 13.8±3.7 for HSV-2 infected and "mock" infected targets respectively).

Figure 9:
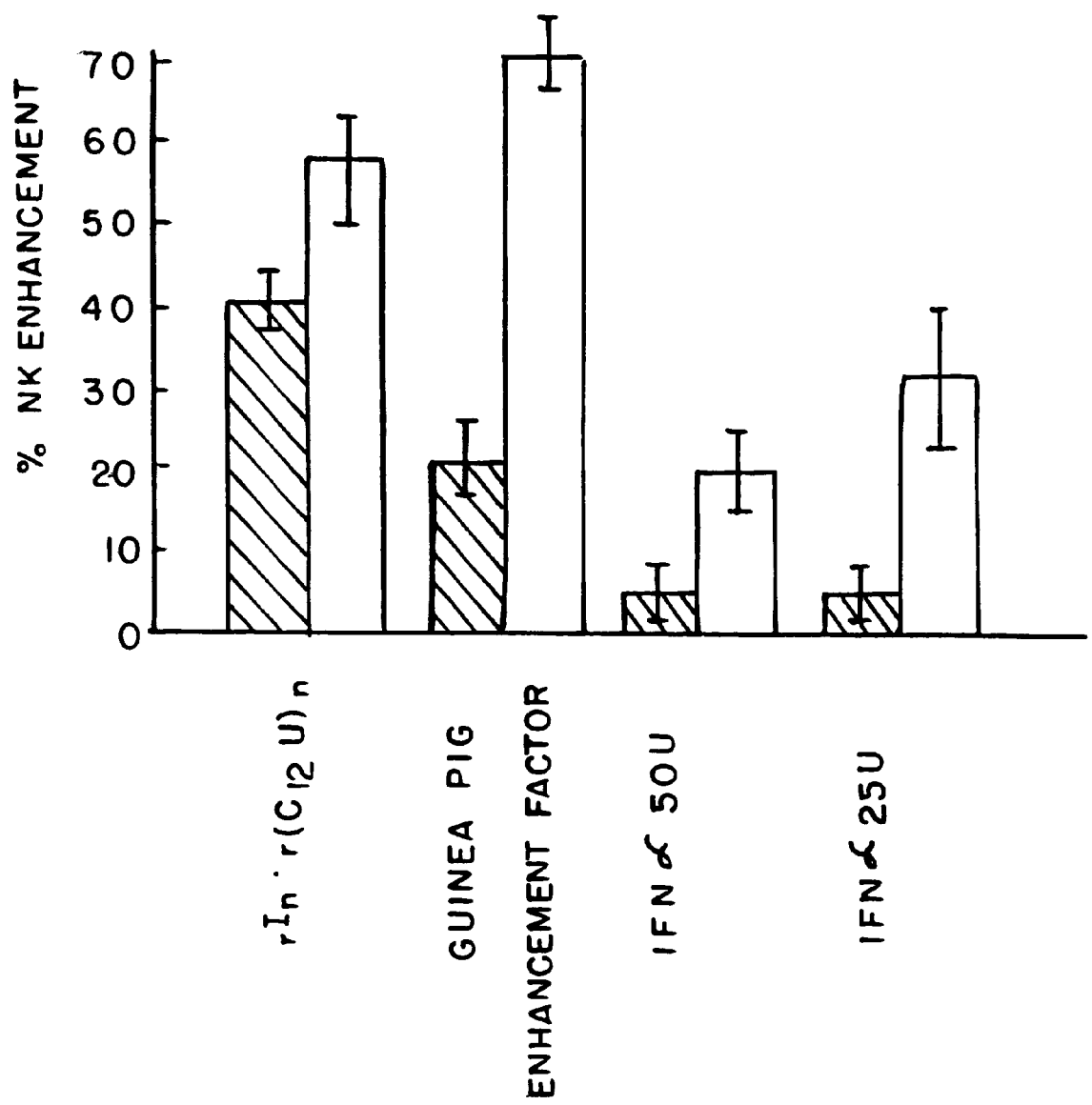
FIG. 9 is a graphical representation of percentage NK enhancement versus polyrI.polyr($C_{12}U$), guinea pig enhancement factor, IFN ($\alpha 50$ and $\alpha 25U$)

Consistent with previous findings, exposire of PBL to polyrI.polyr($C_{12}U$) (2 hrs; 37° C.) caused a significant increase in NK activity (FIG. 9). A similar increase was also observed when PBL were exposed to JH4 supernatant (FIG. 9). However, the highest increase in NK activity was evidenced by PBL obtained from animals treated with polyrI.polyr($C_{12}U$) in vivo (IN; 1.5 $\mu g/g$ weight) and exposed to polyrI.polyr($C_{12}U$) (56±8.8) or JH4 supernatant (68.9±8.2) in vitro. Human IFN$\alpha$ also enhanced the NK activity of PBL from animals treated in vivo with polyrI.polyr($C_{12}U$) but not placebo as shown in FIG. 9.

Numerous studies have suggested that natural mechanisms of resistance, including IFN induction (26–30) activation of macrophages to lyse HSV-2 infected target cells enhancement of NK cell activity, activation of antibody dependent cell cytotoxicity (ADCC) by K cells or neutraphilis play a decisive role during the early stages of a primary HSV infection (27–38). These responses do not require prior sensitization to viral antigen and can be detected as early as 2–4 hours p.i. (29). Furthermore, since only one of two infected individuals develop recurrent HSV-2 lesions although both evidence an apparently normal virus specific immune memory (reviewed in 16,20), it seems reasonable to conclude that the initial stages of a primary infection determine the risk of subsequent recurrent sidease. Therefore, it should be possible to control the severity of HSV infections and the risk of recurrent disease both in the normal and in the immunocompromised host by boosting the capability of infected individuals to mount these initial responses using appropriate immunopotentiating agents.

The salient feature of these investigations is the observation that administration of the nontoxic immunopotentiator polyrI.polyr($C_{12}U$) by a number of routes including the non-invasive IN route, causes a significant reduction in the incidence and severity of primary HSV-2 disease and reduces the risk of subsequent recurrent lesions. Although the exact mechanism of this antiviral activity is unclear, treated animals evidence: (i) decreased virus replication at the site of infection, (ii) reduced titers of latent ganglionic virus and (iii) enhanced NK activity. The data merit discussion from the standpoint of the chemotherapeutic potential of polyrI.polyr($C_{12}U$).

The antiviral activity of polyrI.polyr($C_{12}U$) was studied in both the mouse and guinea pig models of HSV since they differ with respect to pathogenesis and mechanisms of virus persistence. Pharmacologic parameters that were considered relative to the chemotherapeutic potential of the immunopotentiator were its dose, the time of drug administration relative to onset of clinical symptoms onset and the route of drug delivery, as all of them have a definite effect on the ability of the drug to reach critical levels at the site of infection.

Clinical as well as virologic criteria of drug efficacy were considered. Since HSV clinical lesions are variable and therefore their interpretation may suffer from subjective bias, four independent criteria were used for evaluation: (i) lesion score blindly evaluated by two independent observers, (ii) size of the infected as compared to the uninfected rear footpads, (iii) duration of the clinical symptoms defined as above and (iv) the number of animals with clinical symptoms. Virologic criteria of the efficacy of treatment on the primary disease involved determination of virus titers in vesicular fluids obtained at the peak of severity determined according to lesion score and/or footpad size.

The effect of a potential anti-HSV drug on latency and recurrent sidease is of utmost significance. Accordingly the effect of polyrI.polyr($C_{12}U$) treatment was studied on recurrent disease in the guinea pig model and on the establishment of ganglionic latency in the mouse model. Hartley strain guinea pigs were selected, since in this strain 80–95% of the infected animals sustain recurrent episodes the frequency of which is particularly high during the first 4 months after the resolution of the primary lesions (18,19). In this model, animals were followed for clinical symptoms defined according to the criteria used in the primary infection. In the mouse model, virus titers in latently infected ganglia corresponding to the site of virus inoculation were determined at 34 days p.i., when latency had been established.

The chemotherapeutic potential of any drug is at least in part affected by its toxicity. Although previous studies had demonstrated that polyrI.polyr($C_{12}U$) is virtually non-toxic, particularly at the relatively low doses used in these studies (13), some of the routes of administration (i.e. IN) were not previously evaluated. Accordingly, all animals were followed for toxicity related to drug administration including pyrogenicity, listlessness, weight loss and death.

Toxicity studies included groups of 20 mice given 5 IN doses of 400 ug of polyrI.polyr($C_{12}U$) in order to evaluate the chemotheraputic index. There were not toxic effects of any kind in any one of the animals studies in these series, including those given the 400 µg doses (data not shown). In this context it may be significant that previous studies had shown that at this high concentration IV administration of polyrI.polyr($C_{12}U$) causes death within 24 hrs in 40% of the injected animals.

The results of these studies may be summarized as follows. Fifty percent of the placebo treated mice with footpad inoculation, developed paralysis and died while none of the polyrI.polyr($C_{12}U$) treated animals had any evidence of morbidity or mortality. Similarly, treatment was effective against both primary and recurrent disease in the guinea pig model. Dose, time of therapy initiation and the route of drug administration were critical factors in its therapeutic potential. Thus, animals treated with 10 µg/g weight of polyrI.polyr($C_{12}U$) by IP inoculation did not differ from the placebo group with respect to incidence and severity of the primary lesions or the incidence and frequency of recurrent episodes. This was true even if therapy was initiated before HSV-2 infection. On the other hand at 5 µg/g weight IP administration of polyrI.polyr($C_{12}U$) reduced the incidence, duration and severity of the primary lesions and the incidence and frequency of recurrent disease. At this dose polyrI.polyr($C_{12}U$) administration was effective at 8 or 20 hrs. p.i., but by 48 hrs. p.i. its effectiveness was significantly reduced.

From a chemotherapeutic standpoint it is particularly significant that polyrI.polyr($C_{12}U$) was most effective when administered by the non-invasive IN route. Under these conditions the optimal dose was only 1.5 µg/g weight. Therapy in these series was initiated at 6 hrs. p.i. However, its effectiveness at later time intervals has not yet been established. Since reduction in the proportion of animals with recurrent lesions and in the frequency of recurrent episodes experienced by the rest of the animals was observed after a single regime of only 4 IP injection or 5 IN treatments with the drug, it seems reasonable to conclude that unlike anti-HSV drugs now being marketed, continuous treatment with polyrI.polyr($C_{12}U$) might not be required in order to control recurrent episodes.

This is probably related to the effect of polyrI.polyr($C_{12}U$) on the ability of the virus to colonize the ganglia since the virus titers were significantly lower in the ganglia of polyrI.polyr($C_{12}U$) treated as compared to placebo treated animals. However, this was affected by the route of virus inoculation and that of drug administration. Thus, virus titers were reduced in lumbosacral ganglia from mice infected in the footpad and treated IP, but was particularly significant when animals were infected in the pinna of the ear and treated with polyrI.polyr($C_{12}U$) by topical application. The exact interpretation of this interrelationship is not immediately apparent.

However, it probably relates to propensity of the virus to colonize the ganglia and the effective dose of polyrI.polyr($C_{12}U$) that can reach the site of virus replication. Consistent with this interpretation, virus titers were significantly higher in lumbosacral ganglia (infected in the footpad) than in the cervical and trigeminal ganglia (infected in the ear) from the placebo (FIG. 8) suggesting that by comparison to the ear, the treated animals polyrI.polyr($C_{12}U$) treatment was more effective in reducing virus titers in the letter case as indicated in FIG. 8. Similarly, topical polyrI.polyr($C_{12}U$) application was highly effective on the ear lesions as indicated in FIG. 8, but not on footpad lesions that occur in highly keratinized tissue (data not shown).

Treatment of recurrent disease with polyrI.polyr($C_{12}U$) did not shows a significant improvement, although there was a slight increase (12%) in the proportion of animals free of subsequent recurrent episodes. However, this may be due to the fact that treatment of these lesions was initiated 12–24 hrs. after clinical signs first appeared, and this may be somewhat too late in the case of recurrent episodes. Humans on the other hand tend to experience prodomal symptoms 24–48 hrs. before onset of lesions therefore allowing treatment (i.e. intranasal polyrI.polyr($C_{12}U$) administration) to begin at a much earlier time.

Most significantly there was no evidence of toxicity in any one of the animals studied in these series independent of the dose and route of drug administration. Furthermore, toxicity was also not detected in uninfected mice given 4 IN doses of 400 ug of polyrI.polyr($C_{12}U$) (data not shown). We interpret these findings to indicate that at least by the IN route polyrI.polyr($C_{12}U$) has a high chemotherapeutic index.

The mechanism of anti-HSV-2 action of polyrI.polyr($C_{12}U$) is not yet clear. The data indicates that polyrI.polyr($C_{12}U$) therapy does not modulate virus specific antibody titers nor does it increase HSV-2 induced T cell proliferation. On the other hand, it is well established that it induces IFN synthesis (13), and IFN can directly inhibit virus replication at the focus of infection (30) as well as acting as an immunopotentiator by recruiting premature NK cells (39), enhancing NK cytolytic activity and activating macrophages to lyse HSV infected target cells (31). The polyrI.polyr($C_{12}U$) may also activate other cytolytic activities related to HSV infection including ADCC and neutraphilis-mediated cytotoxicity (34,38). Subpopulations of NK cells have been shown to be particularly important in protection from HSV infection (29,35) and the data indicate that polyrI.polyr($C_{12}U$) treatment particularly enhances the cytotoxic activity of NK cells against HSV-2 infected tagets.

Consistent with these interpretations in vitro treatment with polyrI.polyr($C_{12}U$) causes a significant reduction in virus titers only when cells are pre-treated (or treated no later than 1 hour p.i.) suggesting that activity depends on its well established ability to induce IFN synthesis (13). Furthermore, it is found that PBL from placebo treated animals evidence a significantly increased NK activity than PBL from placebo treated animals. The NK activity is even higher when the targets are HSV infected. Consistent with an in vivo immunopotentiating event, the PBL from treated animals evidence a significantly higher enhancement by in vitro polyrI.polyr($C_{12}U$) exposire than the PBL from untreated animals and they even respond to human IFNα thereby overcoming the species specificity barrier.

In preparing the polynucleotide for use in providing a defense system against viral diseases and in order to enhance the immunological defense system of animals including humans, the polyrI.polyr($C_{12}U$) compound (referred to as ribosyl polyinosinic polycytidylic acid—polyuredylic acid copolymer ((12–14:1C:U base ratio)) complex ((1:strand ratio)), also expressed as Poly I.poly $C_{12}U$) is mixed with an anti-bacterial, anti-fungal compound (such as thimerosal, chlorobutano, bensalkonium chloride and/or edetate disodium), and an inorganic salt (such as sodium chloride, potassium chloride, and/or magnesium chloride) to maintain the intactness of the polynucleotide duplex. When this mixture is to be used with an animal including a human, it is mixed with a liquid such as water, and then applied either intranasally and/or topically to the subject in the proper ratio as previously discussed.

The inorganic salts, such as sodium chloride, potassium chloride, and/or magnesium chloride give intactness to the poly nucleotide duplex.

The anti-bacterial anti-fungal compound, such as thimerosal, chlorobutano, bensalkonium chloride, and/or edetate disodium, preserves the polynucleotide duplex, and gives it sterility and shelf life.

If the preservative, that is the anti-bacterial, anti-fungal compound is not mixed in the mixture with polyrI.polyr ($C_{12}U$) then the solution can be applied intranasally, orally, topically, intravenously, and/or intramuscularly.

When the compound polyethyle glycol is mixed with the polyrI.polyr($C_{12}U$) and the inorganic salt in solution, a cream is formed which can be applied topically to the subject being treated.

What is claimed is:

1. A method of treating HSV-2 infection which comprises administering intranasally to a host subject to said infection an effective amount of a ribosyl polyinosinic acid polycytidylic acid-polyuridylic acid copolymer.

2. The method of claim 1 wherein the polynucleotide is administered with an anti-fungal, anti-bacterial compound which functions to preserve the polynucleotide and a therapeutically acceptable inorganic salt selected from the group consisting of sodium chloride, potassium chloride and magnesium chloride.

3. The method of claim 1 wherein the base ratio of said ribosyl polyinosinic acid polycytidylic acid—polyuridylic acid copolymer is 12–14:1 C:U and the strand ratio is 1:1.

4. A method of treating viral diseases by enhancing immunological protection by increasing killer cell activity in an animal having said disease, said method comprising administering an effective amount of a polynucleotide of the formula polyrI.($C_{12}U$) such that natural killer cell activity is increased.

5. A therapeutic composition for treating viral diseases by enhancing immunological protection by increasing natural killer cell activity in an animal in need thereof comprising a polynucleotide of the formula polyrI.polyr($C_{12}U$), an antibacterial, antifungal compound, and an inorganic salt for maintaining the intactness of said polynucleotide, said salt being sodium chloride, potassium chloride or magnesium chloride.

* * * * *